United States Patent
Coughlin et al.

(10) Patent No.: US 6,794,181 B2
(45) Date of Patent: Sep. 21, 2004

(54) METHOD OF PURIFYING LANTIBIOTICS

(75) Inventors: Richard T. Coughlin, Falmouth, ME (US); Joseph H. Crabb, Falmouth, ME (US)

(73) Assignee: ImmuCell Corporation, Portland, ME (US)

(*) Notice: Subject to any disclaimer, the term of this patent is extended or adjusted under 35 U.S.C. 154(b) by 22 days.

(21) Appl. No.: 10/268,037

(22) Filed: Oct. 9, 2002

(65) Prior Publication Data

US 2004/0072333 A1 Apr. 15, 2004

(51) Int. Cl.⁷ .................................................. C12S 3/14
(52) U.S. Cl. ...................... 435/272; 435/68.1; 435/71.3
(58) Field of Search ...................... 435/68.1, 71.1–71.3, 435/212–226, 262, 272; 530/344

(56) References Cited

U.S. PATENT DOCUMENTS

| | | | | |
|---|---|---|---|---|
| 4,900,677 A | * | 2/1990 | Hewitt | 435/259 |
| 5,451,369 A | * | 9/1995 | Daeschel et al. | 422/28 |
| 5,650,320 A | * | 7/1997 | Caufield et al. | 435/252.3 |
| 5,804,684 A | * | 9/1998 | Su | 536/25.4 |

FOREIGN PATENT DOCUMENTS

EP    508371 A1 * 10/1992 ............ C07K/1/14

OTHER PUBLICATIONS

Enzyme Nomenclature. "EC 3.Introduction." and "EC 3.4, peptidases", http://www.chem.qmul.ac.uk/iubmb/enzyme. No date provided.*

Gross et al., J. Am. Chem. Soc. 93: 4634–4635 (1971).

Wilimowska–Pelc et al., Acta Microbiol. Pol A 8: 71–77 (1976).

Chan et al., FEBS Letters 390: 129–132 (1996).

Recio et al., Lait 80: 187–195 (2000).

McAuliffe et al., FEMS Microb. Rev. 25: 285–299 (2001).

* cited by examiner

Primary Examiner—William H. Beisner
(74) Attorney, Agent, or Firm—Pierce Atwood; Kevin M. Farrell

(57) ABSTRACT

Disclosed is a method for purifying a antibiotic from a crude or partially purified solution containing the lantibiotic. In preferred embodiments, the lantibiotic is nisin, although the common structural features of lantibiotics dictate the effectiveness of the disclosed purification methods for other members of the lantibiotic genus. The method includes the step of forming an incubation mixture comprising the solution containing the lantibiotic and a proteolytic enzyme, and incubating the mixture under conditions optimized for selective proteolytic activity.

11 Claims, No Drawings

METHOD OF PURIFYING LANTIBIOTICS

BACKGROUND OF THE INVENTION

Resistance of bacteria to conventional antibiotics used to treat human disease has risen to an international crisis level. A contributing factor has been the widespread use of antibiotics to treat non-life-threatening infections. In recent years, there has been much focus on a promising new class of bacteriocins known as lantibiotics. At present, lantibiotics are being used extensively by the food industry. Lantibiotics have significant commercial value and broad applicability, and practical methods for their production would have a significant economic impact.

Bacteriocins are antimicrobial proteins produced by bacteria that display growth-inhibitory activity against a range of related bacteria. Lantibiotics are polypeptide antimicrobial agents that are produced by certain bacteria and are distinguishable from other antibiotics because of their polypeptide nature and bioactive properties. For example nisin, which is used as a preservative for certain foods, has the unusual amino acid residues, lanthionine and β-methyllanthionine. Nisin, a lysine-rich lantibiotic, is non-toxic to humans and animals, is resistant to high temperatures and is bacteriostatic at very low concentrations. Unfortunately, although lantibiotics are versatile and have unique and advantageous properties, the lack of commercially viable methods for isolation at high purity has limited their utility.

Analysis of the opportunity for the use of nisin by the dairy industry is illustrative of the impact of the lack of cost-effective purification methods. Recently, the potential value of nisin for the milk industry has been recognized, in particular, in connection with the ability of nisin to help fight mastitis infection in cows. The advantage offered by nisin stems, in large part, from its potential to reduce or eliminate "withhold period" rules. The withhold period is a time established, during treatment of mastitis infection of cows, when milk from the infected cow must be discarded. Thus, milk from cow treated for mastitis infection with nisin may enter the fluid milk stream much sooner than traditional antibiotic treatment.

Unfortunately, nisin that is commercially produced by currently available methods of production and purification is considered food grade quality and is not of sufficient purity for pharmaceutical applications. It contains peptide impurities that cause inflammatory reactions when administered to cows. Therefore, due to the lack of efficient alternative methods of purification which could selectively remove such impurities, the value derived from treatment of mastitis with nisin is insufficient to counterbalance current practices. Therefore, a method is needed that improves lantibiotic purity and that is practical to employ on a commercial scale.

To be commercially practical, a purification scheme must be relatively high yield and low cost. With regard to lantibiotic production, it is relatively simple, inexpensive, and routine to culture an organism that either naturally expresses, or has been engineered to express, the desired bacteriocin. Invariably, however, the lantibiotic must be separated from the myriad of proteins that are co-expressed by the organism and that represent contaminating impurities in the initial preparation. Because lantibiotics are polypeptides, and hence share biochemical features with other proteins, the challenge has been in designing a practical protocol that is able to discriminate between the lantibiotic and the other protein or polypeptide impurities.

With few exceptions, the use of proteases or enzymes having protease-like activity is avoided in protein purification protocols in light of the fact that the protein to be purified is typically sensitive to such treatment. For example, trypsin can not be used in a method for purifying a peptide that contains internal lysine or arginine residues because trypsin recognizes such residues and cleaves a protein or polypeptide containing such residues at their location. Moreover, purity and recovery of a protein, using a protease-based purification scheme, can be inversely related. This means that, under conditions that favor increased recovery of the protein of interest, impurities tend to remain insufficiently digested.

SUMMARY OF THE INVENTION

The present invention relates to a method for purifying a lantibiotic from a crude or partially purified solution containing the lantibiotic. In preferred embodiments, the lantibiotic is nisin, although the common structural features of lantibiotics govern the effectiveness of the disclosed purification methods for other members of the lantibiotic genus. The method includes the step of forming an incubation mixture comprising the solution containing the lantibiotic and a proteolytic enzyme, and incubating the mixture under conditions which are optimized for the selective proteolytic activity of the enzyme, thereby digesting non-lantibiotic protein, polypeptide and peptide components of the solution containing the lantibiotic, while leaving the lantibiotic substantially undigested.

DETAILED DESCRIPTION OF THE INVENTION

Lantibiotics are a group of ribosomally synthesized, post-translationally modified peptides containing unusual amino acids. Such amino acids include the thioether amino acids lanthionine (Lan) and/or MeLan, in addition to a number of modified residues, such as 2,3-didehydroalanine (Dha) and 2,3-didehydrobutyrine (Dhb). The presence and influence of these residues on the structure and activity of lantibiotics has been the subject of significant research efforts It has been observed, for example, that the sequence-specific dehydration of serine (to Dha) and threonine (to Dhb) results in modified amino acids with electrophilic centers which can react with neighboring nucleophilic groups. The thioether lanthionine is formed when the double bond in Dha is attacked by the thiol (—SH) group of a neighboring cysteine residue. As a consequence of the presence of these intramolecular bridges, lantibiotics are polycyclic structures containing a number of lanthionine rings. The presence of these lanthionine rings is thought to be essential for a number of important lantibiotic properties including, for example, maintenance of peptide rigidity and resistance to thermal inactivation.

The present invention is based on Applicants' surprising discovery that a crude or partially purified preparation of a lantibiotic can be subjected to protease treatment under conditions which result in selective proteolytic activity against protein or polypeptide impurities, without measurable proteolysis of the lantibiotic. The use of such conditions represents an effective method for the purification of a lantibiotic.

The prior art teaching which relates to the sensitivity of lantibiotics to protease digestion is mixed. Many of these reports relate specifically to the well-studied lantibiotic, nisin. For example, Gross et al. (*J. Am. Chem. Soc.* 93(19) (1971) 4634–4635) reported that nisin was trypsin-sensitive. A contradictory report was later published by Wilimowska-Pelc (Acta Microbiol. *Pol A* 8(1) (1976) 71–77). More recently, Chan et al. (*Int. Food Microbiol.* 390 (2001) 267–281) reported that nisin is subject to tryptic digestion, but at a reduced rate. In summary, one of skill in the art, familiar with relevant teaching of the prior art, could not have predicted with any degree of certainty that it would be possible to identify conditions under which non-lantibiotic protein, polypeptide and peptide impurities present in a crude or partially purified lantibiotic containing solution could be selectively degraded by the action of a proteolytic enzyme, without substantially degrading the lantibiotic present in the solution. This discovery is particularly important given the long-felt need for an improved, cost-effective, high purity method for lantibiotic purification which yields a lantibiotic preparation suitable for pharmaceutical use.

The conditions for protease digestion determined to be effective in connection with the present invention can be characterized as selective. That is, the conditions established for the incubation that includes the impure lantibiotic and a proteolytic enzyme are conditions under which the proteolytic enzyme operates selectively to degrade non-lantibiotic impurities. Parameters which can be varied to modulate these selective conditions include altered pH ranges, reduced protease to lantibiotic ratios, reduced temperatures, etc. This listing of parameters which can be altered to optimize the selective operation of the proteolytic enzyme is not intended to be comprehensive as those skilled in the art will recognize other parameters that can be altered to effect the desired goal.

One of skill in the art can readily determine optimal conditions for a particular proteolytic enzyme. If produced commercially, the manufacturer typically provides such information in packaging materials shipped with the enzyme. Alternatively, it is a matter of routine experimentation to empirically determine such conditions.

Optimal conditions, however, are not necessarily selective conditions. Under incubation conditions which are optimal for a given proteolytic enzyme, both the lantibiotic, as well as protein or polypeptide impurities, may be degraded. Generally speaking, selective conditions are empirically determined. A starting point for such a determination is the manufacturer's recommended optimal condition. If, under these conditions, both lantibiotic and impurities are degraded, the conditions may be "de-tuned" arrive at the selective conditions. For example, as discussed below, the reported optimal pH for the enzyme trypsin has been reported to be about 8.0. However, the optimized selective conditions described in the Specification include, under otherwise identical incubation conditions, a pH within the range of about 5.50 to about 6.25.

In the Exemplification section which follows, the extensively studied lantibiotic-nisin was employed. However, as indicated above, representatives of the lantibiotic genus share a number of structural features, some of which have been identified as contributing to their relative resistance to proteolysis. Lanthionine rings, for example, have been specifically cited in this regard. Thus, white the Exemplification section focuses primarily on the lantibiotic nisin, the principles established herein would be expected to apply to all lantibiotics due to the presence of their defining structural characteristics. Other lantibiotics include, for example, subtilin, epidermin, gallidermin, mutacin, pep5, epicidin, epilancin, lacticin, cytolysin, staphylococcin, salvaricin, lactocin, streptococcin, sublancin, carnocin, variacin, cypemycin, connamycin, duramycin, ancovenin, mersacidin and actagurdine.

The methods of the present invention are particularly well-suited to the proteolytic purification of a lantibiotic present in crude or partially purified fermentation broth. In the fermentation of nisin, for example, peptide analysis by GC/MS/MS has identified over 40 peptides that co-purify with nisin. The Exemplification section which follows clearly demonstrates the effectiveness of trypsin in the degradation of the co-purifying impurities.

With respect to the proteolytic activity of trypsin, the optimal pH has been reported to be about 8.0. Under otherwise identical incubation conditions, the optimized selective conditions described in the Specification include a pH within the range of about 5.50 to about 6.25. Similar conditions fall within the selective range for other proteases including, for example, endopeptidase Arg-C, thermolysin, V8 protease, subtilisin, proteinase K, pepsin, papain, clostripain, lysyl endopeptidase, endopeptidase Asp-N, enterokinase, or Factor Xa. Preferably, conditions for selective digestion of nisin impurities by these other proteases comprise pH in the range of about 5.50 to 6.25. In the preferred embodiment, the pH is 5.90. With respect to pepsin, a pH of 3.5 is within the selective limits.

The selective protease digestion conditions, as defined by the selective digestion of non-lantibiotic impurities, can be achieved in a variety of ways. This can include, for example, low protease to lantibiotic ratio, decreased temperature, altered pH, etc. The various relevant parameters can be altered independently or in combination.

Following completion of proteolytic digestion, it may be desirable to remove the protease. A particularly convenient method for facilitating removal of the protease following digestion is to provide the protease attached to a solid support (e.g., an agarose or a magnetic bead). In this format, the solid support is easily separated from the incubation mixture following digestion. Alternatively, simple sizing column steps may be employed to effect removal of the protease. Other techniques for removing proteases following proteolytic digestions are known in the art, including chromatography techniques such as those based on affinity, ion exchange, and hydrophobicity.

It should be noted that although it may be desirable to remove the proteases after the impurities have been digested, it is not necessary to do so for all applications. For example, if the purified lantibiotic is intended to be consumed with a food product, the protease may not have to be removed in order to satisfy relevant regulations. For example, trypsin has been granted Generally Recognized As Safe (GRAS) status for certain food applications.

EXEMPLIFICATION

Nisin Is Sensitive to Proteolysis by Trypsin at Neutral to Slightly Alkaline pH and High Trypsin to Nisin Ratio Nisin has two internal lysine residues that are potential targets of the proteolytic enzyme trypsin. To determine whether nisin could be digested by trypsin, a digestion reaction mixture was prepared where a nisin preparation, partially purified nisin from a fermentor run, was exposed to trypsin under conditions optimal for trypsin activity. These conditions included a reaction pH of 7.0 and a nisin to trypsin ratio of about 10:1 (w/w). Samples were incubated at 30° C. and aliqoutes were removed for analysis every 24 hr, beginning at time zero. Coomasie blue staining of SDS-PAGE demonstrated that, under the conditions employed, nisin was degraded by trypsin. Moreover, quantitative HPLC analysis of nisin at the various time points revealed that nisin recovery began to diminish by 24 hours following exposure to trypsin. After 96 hr of treatment, more than 90% of nisin was degraded.

Nisin is Resistant to Trypsin Digestion at Low pH and Low Trypsin to Nisin Ratio Peptide analysis has identified over 40 peptides that co-purify with nisin. All of these peptides have been identified as being products of *Lactococcus fermentation*. Since it was determined that nisin, at neutral to slightly alkaline pH and high trypsin to nisin ratios, is subject to proteolysis by trypsin, conditions were altered in an attempt to identify conditions under which trypsin would not degrade nisin but would degrade the peptide impurities in the nisin sample. Reaction mixtures containing nisin preparations, at a concentration of 11 mg/ml, and USP grade trypsin at a concentration of 27.5 µg/ml, were incubated overnight at room temperature (400:1 w/w). The pH of the mixtures ranged from 5.25 to 6.5. While minimal hydrolysis of both nisin and impurities occurred below pH 5.50, quantitative HPLC analysis indicated that recovery of nisin was best at or below pH 6.25. These results indicated that conditions involving dilute trypsin and pH between 5.50 and 6.25 are optimal for removal of peptide impurities from nisin preparations with minimum loss of nisin to tryptic digestion.

To further optimize the conditions for removal of peptide impurities from nisin preparations by tryptic digestion, two liters of partially purified nisin was prepared at 4.55 mg/ml and incubated with 25 mg of USP grade trypsin for 16 hrs at 30° C. in 10 mM citric acid, pH 5.80. HPLC analysis revealed an overall hisin recovery of about 95%. Moreover, subsequent removal of trypsin using a molecular weight cut off membrane yielded a recovery of 87.5% nisin and 0.38% trypsin.

To determine whether insoluble trypsin treatment of nisin preparations was also effective in digestion of impurities, but not nisin itself, 1.6 liters of partially purified nisin prepared at 9.55 mg/ml was treated with 1.6 ml of TPCK treated insoluble trypsin bound to beaded agarose. After 6 hr of incubation at 30° C., and following removal of insoluble trypsin by centrifugation, the overall nisin recovery was about 90%.

Trypsin-treated Nisin Retained Antimicrobial Activity

Treatment of nisin preparations with trypsin, under the conditions described above, does not affect the physical structure of nisin as judged by mobility on a reverse phase HPLC column or migration by SDS-PAGE. To confirm that the biological activity of nisin is also unaltered, in vitro bactericidal activity assay was performed. Trypsin-treated nisin was analyzed for antibacterial activity against a mastitic isolate of Streptococcus agalactiae (strain #20) in a 96 well plate assay and bacterial growth was read as absorbance readings on an ELISA reader. These experiments demonstrated that the antimicrobial activity of trypsin-treated nisin is not substantially different than the activity of the control, untreated nisin.

Trypsin Treatment Reduces the Inflammatory Factors Present

Bovine intra-mammary infusion of impure nisin stimulates the production of high levels of somatic cells in milk as part of an inflammatory reaction. As shown in Table 1, non-mastitic cows treated with an infusion of 30 mg partially purified nisin have somatic cell counts that are greatly elevated. In contrast, somatic cell count of milk from quarters treated with an infusion of trypsin-purified nisin is much lower and is not statistically different from quarters treated with buffer alone.

Other Proteases Exhibit Selective Activity Towards Impurities Over Nisin

Nisin is comparatively resistant to proteolysis by trypsin under the optimized conditions described above. To determine whether nisin is also resistant to other proteolytic enzymes under similar conditions, partially purified nisin was exposed to pepsin, thrombin, V8 protease (Endo Gluc), subtilisin, papain, thermolysin, or clostripain at pH 5.80. Pepsin exposure was also performed at pH 3.50. The results showed that nisin was resistant to proteolytic digestion by the enzymes. Pepsin at pH 5.80 and thrombin appeared ineffective against the impurities as well. At pH 3.50 pepsin was effective at digesting nisin impurities, but did not digest nisin. These results demonstrate that, under the low pH conditions and nisin to protease ratios described for trypsin treatment, other proteases also exhibit selective activity towards impurities over nisin.

Methods

Trypsin Digestion

Tryptic digestion of nisin (50 mg) was carried out in 50 ml of a buffer consisting of 25 mM sodium acetate, 6 mM Tris acetate, 5 mM $CaCl_2$, and pH 7.0. One ml of USP grade trypsin (5 mg/ml) was added followed by incubation at 30° C. Thereafter, 500 µl aliqouts of trypsin were added at times 24, 48, 72, and 96 hours. At each time point in the experiment, 2 ml aliquots were removed for further analysis, of which 100 µl was immediately plated on blood agar plates for determination of contamination. The remaining 1.8 ml was stored at −20° C. until the end of experiment for SDS-PAGE and HPLC analysis.

Protease Digestion

For treatment of nisin with soluble trypsin, 2 liters of partially purified nisin from a fermentation product was prepared at 4.55 mg/ml in 10 mM citric acid buffer and 5 mM $CaCl_2$. After addition of 25 mg of USP grade trypsin, the reaction mixture was incubated overnight at 30° C. The weight ratio of nisin to trypsin was approximately 400:1 (w/w). NaOH was used to adjust the pH of the digestion reaction to a range between 5.25 to 6.50. Nisin recovery and purity was determined by SDS-PAGE and HPLC. Digestion reactions were terminated by lowering the pH to 3.0 using 3N HCl. Based on the results, a pH of 5.80 was selected and used in all subsequent reactions involving other proteases.

Digestion experiments using pepsin (EC3.4.23.1), thrombin (EC3.4.21.5), V8 protease (EC3.4.21.19), subtilisin (EC3.4.21.62), papain (EC3.4.22.2), thermolysin (EC3.4.24.27), and clostripain (EC3.4.22.8) were performed essentially as described for trypsin and at pH 5.80. Pepsin digestion was also performed at pH 3.50. For trypsin digestions using trypsin linked to a solid matrix (e.g. insoluble trypsin), 1.6 liters of partially purified nisin was prepared at 9.5 mg/ml in 10 mM Tris HCl and pH 5.50. Following the addition of 1.6 ml of TPCK-treated trypsin bound to beaded agarose (Sigma Chemical company), the reaction mixture was incubated at 30° C. for 6 hours with frequent agitation. Insoluble trypsin was removed by centrifugation at approximately 4000× g for 7 minutes. The resultant supernatant containing nisin was prepared for HPLC analysis.

Mammary Infusion

Non-mastitic cows were treated with an infusion of vehicle, untreated, and trypsin-treated nisin (30 mg/10 ml) in the quarter after the $4^{th}$, $5^{th}$, and $6^{th}$ milkings. The somatic cell count of the milk was recorded before, during, and after milking. High somatic cell counts were indicative of an inflammatory reaction. Statistical analysis was carried out using two sided t-Test comparisons with unequal variance.

Biological Activity of Nisin

Nisin activity was determined using an antibacterial assay against a mastitic isolate of *Streptococcus agalactiae* (IC 20) in a 96 well plate assay. Test samples were serially diluted into M17 10% lactose medium and then mixed with an equal volume of $10^4$ cfu/ml. After 66 hr of incubation at room temperature, the plates were read on an ELISA reader at 450 nm. Wells containing bacterial growth gave high absorbance readings. The data was analyzed using a four-parameter curve-fitting software.

TABLE 1

Reduced inflammation in trypsin-treated nisin

| Milking [Treatments given after 4th, 5th, 6th] | Somatic Cell Count of Quarter Milk (X1000) | | | t-Test Comparison (Two sided with unequal variance) | |
|---|---|---|---|---|---|
| | Mean of vehicle control | Mean of trypsin/ nisin group | Mean of nisin starting material group | Vehicle control vs. trypsin/ nisin group | Vehicle control vs. nisin starting material group |
| 1 | 25 | 10 | 23 | 0.196 | 0.775 |
| 2 | 33 | 22 | 37 | 0.372 | 0.845 |
| 3 | 72 | 23 | 30 | 0.376 | 0.696 |
| 4 | 21 | 21 | 24 | 0.395 | 0.644 |
| 5 | 58 | 54 | 2360 | 0.944 | 0.018 |
| 6 | 105 | 187 | 2269 | 0.439 | 0.155 |
| 7 | 133 | 300 | 5787 | 0.382 | 0.000 |
| 8 | 61 | 148 | 2842 | 0.360 | 0.008 |
| 9 | 88 | 106 | 2325 | 0.671 | 0.000 |
| 10 | 86 | 82 | 879 | 0.664 | 0.000 |
| 11 | 69 | 103 | 1066 | 0.589 | 0.000 |
| 12 | 51 | 81 | 113 | 0.467 | 0.284 |
| 13 | 48 | 60 | 514 | 0.832 | 0.001 |
| 14 | 39 | 36 | 172 | 0.907 | 0.092 |
| 15 | 57 | 53 | 294 | 0.692 | 0.045 |
| 16 | 30 | 37 | 107 | 0.889 | 0.202 |
| 17 | 39 | 40 | 128 | 0.825 | 0.123 |
| 18 | 28 | 41 | 80 | 0.691 | 0.210 |

What is claimed is:

1. A method for purifying nisin, the method comprising:

a) providing a solution containing nisin;

b) providing a prcteolytic enzyme which is known to cleave a sequence element contained within the nisin sequence; and c) forming an incubation mixture comprising the solution containing nisin and the proteolytic enzyme of step b), and incubating the mixture under conditions which are optimized for selective degradation of non-nisin protein or polypeptide impurities, while leaving the nisin substantially undigested.

2. The method of claim 1 further comprising the step of removing or inactivating the proteolytic enzyme following digestion.

3. The method of claim 1 wherein the provided solution of step a) is a product of fermentation.

4. The method of claim 1 wherein the proteolytic enzyme is trypsin.

5. The method of claim 4 wherein the conditions optimized for selective degradation comprise a pH of between 5.5 and 6.25.

6. The method of claim 1 wherein the proteolytic enzyme is selected from the group consisting of trypsin, endopeptidase Arg-C, thermolysin, V8 protease, subtilisin, proteinase K, clostripain, lysyl endopeptidase, papain, endopeptidase Asp-N, enterokinase, Factor Xa, and chymotrypsin.

7. The method of claim 6 wherein the conditions optimized for selective activity comprise a pH of between 5.5 and 6.25.

8. The method of claim 1 wherein the proteolytic enzyme is pepsin.

9. The method of claim 8 wherein the conditions optimized for selective activity comprise a pH of greater than about 4.5.

10. The method of claim 1 wherein the proteolytic enzyme is linked to a solid support.

11. The method of claim 1 wherein the effective amount of the proteolytic enzyme is about 400/1 (w/w) nisin/ proteolytic enzyme.

* * * * *

UNITED STATES PATENT AND TRADEMARK OFFICE
CERTIFICATE OF CORRECTION

PATENT NO.    : 6,794,181 B2
DATED         : September 21, 2004
INVENTOR(S)   : Richard T. Coughlin and Joseph H. Crabb It is certified that error appears in the above-identified patent and that said Letters Patent is hereby corrected as shown below:

Column 7,
Line 36, delete "prcteolytic" and substitute therefore -- proteolytic --.

Signed and Sealed this

Twenty-second Day of February, 2005

JON W. DUDAS
*Director of the United States Patent and Trademark Office*